United States Patent
Knoll et al.

(10) Patent No.: US 8,506,496 B2
(45) Date of Patent: Aug. 13, 2013

(54) METHOD AND APPARATUS TO DETERMINE THE END OF THE SYSTOLIC PART OF A PRESSURE CURVE

(75) Inventors: Reinhold Knoll, Munich (DE); Ulf Borg, Longmont, CO (US); Ulrich Pfeiffer, Munich (DE)

(73) Assignee: Edwards Lifesciences IPRM AG, Nyon (CH)

( * ) Notice: Subject to any disclaimer, the term of this patent is extended or adjusted under 35 U.S.C. 154(b) by 342 days.

(21) Appl. No.: 12/744,772

(22) PCT Filed: Nov. 24, 2008

(86) PCT No.: PCT/EP2008/009942
§ 371 (c)(1), (2), (4) Date: Nov. 3, 2010

(87) PCT Pub. No.: WO2009/068233
PCT Pub. Date: Jun. 4, 2009

(65) Prior Publication Data
US 2011/0040195 A1    Feb. 17, 2011

(30) Foreign Application Priority Data
Nov. 28, 2007  (DE) .................. 10 2007 057 235

(51) Int. Cl.
*A61B 5/02* (2006.01)
*A61B 5/04* (2006.01)

(52) U.S. Cl.
USPC ........................ 600/485; 600/500; 600/513

(58) Field of Classification Search
USPC ................... 600/485, 481, 509, 513
See application file for complete search history.

(56) References Cited

U.S. PATENT DOCUMENTS

| | | | |
|---|---|---|---|
| 5,400,793 A | 3/1995 | Wesseling |
| 5,450,850 A | 9/1995 | Iinuma |
| 6,071,244 A | 6/2000 | Band |
| 6,120,442 A | 9/2000 | Hickey |
| 6,315,735 B1 | 11/2001 | Joeken |
| 6,348,038 B1 | 2/2002 | Band |
| 2003/0216653 A1 | 11/2003 | Poliac et al. |
| 2005/0124903 A1 | 6/2005 | Roteliuk |
| 2005/0124904 A1 | 6/2005 | Roteliuk |
| 2006/0167361 A1 | 7/2006 | Bennett et al. |

FOREIGN PATENT DOCUMENTS

| | | |
|---|---|---|
| WO | 2005112746 | 1/2005 |
| WO | 2007109059 | 9/2007 |

OTHER PUBLICATIONS

Wesseling, A Simple Device for the Continuous Measurement of Cardiac Ouput, Adv. Cardiovasc Phys, 1983, 5, 26-52.
International Search Report, PCT/EP2008/009942, May 28, 2009.

*Primary Examiner* — Navin Natnithithadha
*Assistant Examiner* — Etsub Berhanu
(74) *Attorney, Agent, or Firm* — Michael Crapenhoft

(57) ABSTRACT

The invention relates to a method and an apparatus for determining the systolic phase interval (SP) of an arterial pressure curve with a starting point (t0) of the systolic phase interval (SP) and an end point (tN) of the systolic phase interval (SP) wherein a QT interval is defined as the start of the Q wave and the end of the T wave in the hearts electrical cycle and wherein the determination of the end point (tN) of the systolic phase interval (SP) is restricted to the measured points of arterial pressure which fulfill the condition that the difference in time between the end point (tN) to be determined of the systolic phase interval (SP) and the starting point (t0) of the systolic phase interval (SP) is smaller than the QT interval.

6 Claims, 3 Drawing Sheets

Figure 1:
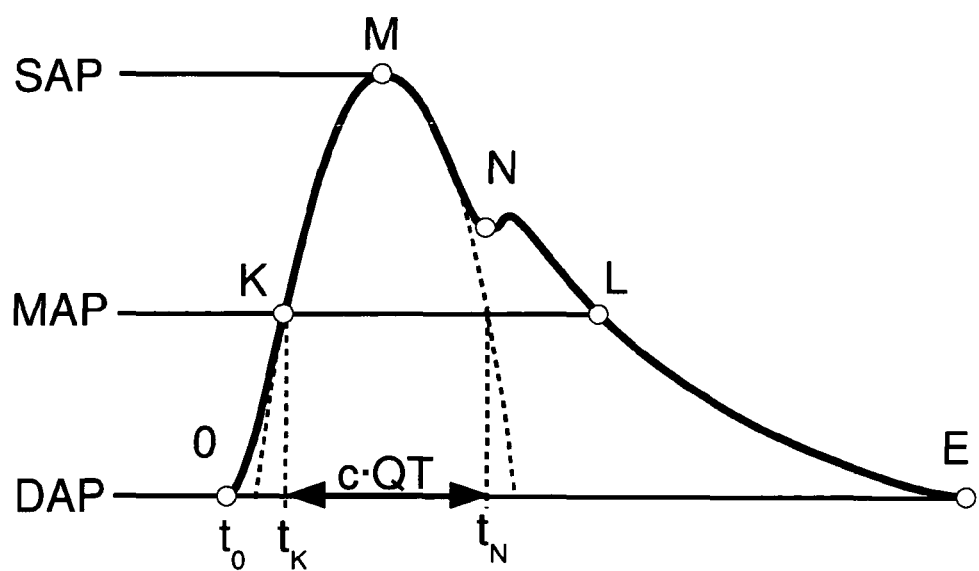

METHOD AND APPARATUS TO DETERMINE THE END OF THE SYSTOLIC PART OF A PRESSURE CURVE

The present application is a U.S. National Phase of International Patent Application No. PCT/EP2008/009942, which was filed Nov. 24, 2008, which claims the benefit of priority of DE 10 2007 057 235.4, which was filed Nov. 28, 2007. Each of these applications is incorporated by reference in its entirety.

The invention relates to a method and an apparatus to determine the end of the systolic part of a pressure curve especially intended for pulse contour algorithms.

From the arterial pressure curve different blood circulation parameters e.g. stroke volume, systemic vascular (i.e. peripheral) resistance and arterial compliance can be determined. The determination could be performed with well-known pulse contour methods. For example: Wesseling, A simple device for the continuous measurement of cardiac output, Adv cardiovasc Phys 1983 5 26-52; Wesseling U.S. Pat. No. 5,400,793; Band U.S. Pat. No. 6,071,244, U.S. Pat. No. 6,348,038; Joeken U.S. Pat. No. 6,315,735; Roteliuk US 20050124903, US 20050124904.

The stroke volume and hence the blood flow could be derived from the arterial blood pressure curve on the base line of empirical rules e.g. from the area under the systolic part of the pressure curve. Another method involves adjusting the parameters of a mathematical circulation model until the resulting pressure curve of the model agrees with the measured pressure curve. As an example, the arterial system could be described by a three element model consisting of arterial compliance, an arterial impedance and a peripheral resistance. These model elements are not adapted to an individual patient but rely on statistical observations—sometimes dependent on age, gender, weight and/or height.

The duration of the systolic phase, i.e. the phase when blood is pushed out of the heart, has a substantial direct or indirect influence on these pulse contour algorithms. The beginning of the systolic phase could be clearly detected by a sudden pressure increase starting nearby the diastolic (arterial) pressure DAP i.e. the minimum pressure within a beat cycle. The end of the systolic phase is indicated by the dicrotic notch which results from a minimal retrograde aortic blood flow during closing of the aortic valve. This is a pressure pattern typical for the aortic valve closing.

However, the dicrotic notch may be difficult to detect. With over-damped pressure signals the appearance of the dicrotic notch could even be hidden. Sometimes the typical shape of the dicrotic notch could be poorly differentiated from frequently existing disturbances e.g. signal reflections or resonances caused by under-damped pressure signals. A falsely determined dicrotic notch could cause large errors e.g. in the calculated stroke volume.

Some purely empirical methods (Volume U.S. Pat. Nos. 6,071,244, 6,348,038, Roteliuk US 20050124903, US 20050124904) are computed simply without the need of identifying the systolic phase. However, these methods suffer from difficulties to respond to parameter changes of the blood circulation system e.g. of the heart rate.

Thus, it is an objective of the present invention to provide for a robust and accurate method and an apparatus to determine the end of the systolic part of a pressure curve especially intended for pulse contour algorithms.

The object of the invention is achieved by a method for determining the systolic phase interval (SP) of an arterial pressure curve, especially the pressure curve induced by a heart, with a starting point ($t_0$) of the systolic phase interval (SP) and an end point ($t_N$) of the systolic phase interval (SP) wherein a QT interval is defined as the start of the Q wave and the end of the T wave in the hearts electrical cycle and wherein the determination of the end point ($t_N$) of the systolic phase interval (SP) is restricted to the measured points of arterial pressure which fulfill the condition that the difference in time between the end point ($t_N$) to be determined of the systolic phase interval (SP) and the starting point ($t_0$) of the systolic phase interval (SP) is smaller than the QT interval.

The QT interval is a measure of the time between the start of the Q wave and the end of the T wave in the heart's electrical cycle. The QT interval is dependent on the heart rate in an obvious way (the faster the heart rate, the shorter the QT interval) and has to be adjusted to aid interpretation.

Within an ECG, the Q wave represents the start of depolarization of the ventricles. The T wave represents the repolarization of the cardiac ventricles. It is known e.g. from Bazett, that the QT interval is closely related to the heart rate with little variations $$QT := t_T - t_Q = f(HR)$$

There are several other formulas published which could be used e.g. from Rautaharju $$QT = \frac{656}{1 + HR/100}$$

or Hegglin-Holzmann $$QT = 390 \cdot \sqrt{60/HR}$$

with the QT interval given in milliseconds and the heart rate HR in beats per minute.

The point Q appears at $t_Q$ a short time before the start of the systolic phase at $t_0$. For a rough estimation, the time difference ($t_0 - t_Q$) could be neglected. The point T appears at $t_T$ after the end of the systolic phase at $t_N$. Hence, the systolic phase ($t_N - t_0$) must be shorter than the QT interval ($t_T - t_Q$).

$$t_N - t_0 \leq QT$$

Normal values for the QT interval are between 0.30 and 0.44 (0.45 for women) seconds. The QT interval can also be measured by different methods such as the threshold method in which the end of the T wave is determined by the point at which the component of the T wave merges with the isoelectric baseline or the tangent method in which the end of the T wave is determined by the intersection of a line extrapolated from the isoelectric baseline and the tangent line which touches the terminal part of the T wave at the point of maximium downslope.

In another embodiment of the present invention a method is provided, wherein the end point ($t_N$) of the systolic phase interval (SP) is determined as the sum of the time interval between the starting point ($t_0$) of the systolic phase interval (SP) and the point of time ($t_K$), where the mean arterial pressure (MAP) is reached for the first time following the starting point ($t_0$) of the systolic phase interval (SP) and the product of a factor (c) with the QT interval (QT), wherein the factor (c) is a value between 0.25 and 0.8, especially wherein the factor (c) fulfills the condition $$c = \sqrt{\frac{SAP - MAP}{SAP - P_0}}$$

with the maximum arterial pressure (SAP) and the mean arterial pressure (MAP) and the base line pressure (P0), which is approximately equal to the pressure within the left ventricle as well as within the left atrium at the time of the start of the Q wave and the end of the T wave in the hearts electrical cycle.

Thus, even without a special notch detection algorithm, the QT interval ($t_T-t_Q$) is preferably used as a rough estimate for the duration of the systolic phase ($t_N-t_0$). For further improvement, the QT interval may be shortened by a certain factor c which is greater than 0.25 and less than one, e.g. 0.8. At the time of point Q and point T, the pressure within the left ventricle is at the same level $P_0$ as within the left atrium. This pressure could be roughly substituted by an assumed, situation dependent value or roughly substituted by the central venous pressure or by zero. Because the notch is close to the mean arterial pressure and a parallel shifted parabola could be assumed, the factor c could preferably be estimated by $$c \approx \sqrt{\frac{SAP - MAP}{SAP - P_0}}$$

Thus, the time of the end of systolic phase becomes $$t_N = t_K + c \cdot QT$$

The estimated pressure area between arterial pressure AP and diastolic pressure DAP—from start of the systolic phase $t_0$ until the time estimated from shortened QT interval after first intersection of the pressure curve with the mean arterial pressure $t_K$—will be roughly proportional to the stroke volume SV.

$$SV = const \cdot \int_{t_0}^{t_N} (AP - DAP) dt$$

This is a very robust algorithm that tracks parameter changes much better and much more robustly than previous algorithms with or without notch detection.

In a further embodiment of the invention, a method is provided, wherein the search for the end point (tN) of the systolic phase (SP) is restricted to the interval between the point of time of the maximum arterial pressure (tM) and the end of the QT interval (tT).

In a further embodiment of the invention, a method is provided, wherein the search for the end point (tN) of the systolic phase (SP) is restricted to the region where the measured arterial pressure is higher than the mean arterial pressure (MAP). The mean arterial pressure is the integral of the arterial pressure over a beat cycle divided by the beat duration.

Measured with ECG or calculated from the heart rate HR the QT interval could preferably be estimated and used to improve the identification of the systolic phase of the arterial pressure curve. Searching for the dicrotic notch, could be restricted from the time of the maximum pressure $t_M$ until the end of the QT interval $t_T$ or until the time of the QT distance after the start of the systolic phase. Searching the notch could be further restricted to the region where arterial pressure is greater than mean arterial pressure.

This will significantly reduce false notch identifications and could be applied to any notch detection algorithm e.g. the method disclosed in EP1746931.

In a further embodiment of the invention, a method is provided, wherein the end point (tN) of the systolic phase interval (SP) is determined by the intersection of two fitted functions with a first function of parabolic nature (y1) and a second function of exponential nature (y2).

In a further embodiment of the invention, a method is provided, wherein the first function of parabolic nature (y1) is fitted to the pressure curve defined by the measured pressure curve of the systolic phase and the second function of exponential nature (y2) is fitted to the pressure curve defined by the measured pressure curve of the diastolic phase.

The end of the systolic phase could preferably be estimated more accurately by the following procedure. A function prototype $y_1$ could be fitted to the pressure curve of the systolic phase—from the start of the systolic phase (point 0 at $t_0$) until a preliminary point for the end of the systolic phase (point N at $t_N$). The fitting is done in a way, that the time distance of the curve points at the $P_0$ pressure level becomes equal to the QT interval. Preferably a parallel shifted parabola function is used as function prototype $y_1$ $$y_1 = SAP - 4 \cdot \frac{SAP - CVP}{QT^2} \cdot (t-a)^2$$

The parallel shifting is preferably done with a coordinate transformation $$t \rightarrow t + b \cdot y$$

The parameters a and b are then preferably adjusted to provide the least square of residuals $(AP-y_1)^2$.

Thus, the fitted curve could be regarded as a surrogate for the pressure within the left ventricle.

Another function prototype $y_2$ could be fitted to the pressure curve of the diastolic phase—from end-systolic phase (point N at $t_N$) to beginning of the next systolic phase (point E at $t_E$). The fitting is preferably done in a way that the point N will be on the previously fitted curve $y_1$.

Preferably an exponential decay function is used as function prototype $y_2$.

$$y_2 = CVP + (y_1(t_N) - CVP) \cdot \exp\left(-\frac{t-t_N}{d}\right)$$

The parameter d is then preferably adjusted to provide the least square of residuals $(AP-y_2)^2$.

The preliminary point N for the end-systolic phase is shifted starting from point T until the maximum arterial pressure point M. The final point N for the end of systolic phase will be the one, which gives the best fitting results e.g. the fittings with the least sum of residuals $(AP-y_1)^2+(AP-y_2)^2$.

This end systolic point could be also useful for model flow algorithms. For a certain model, e.g. the 3-element model, a certain flow prototype function—e.g. an asymmetric triangle profile—is assumed. The flow duration is set according to the previous estimated systolic duration whereas the flow amplitude is shifted until best fit of the pressure curve is achieved.

The object of the invention is also achieved by an apparatus, comprising an input (10) for signals related to a pressure, especially an arterial pressure, a time element (12) to determine the time related to the signals a processor (15) for computing the systolic phase interval (SP) of an arterial pressure curve of a heart wherein the processor (15) is adapted to determine a starting point (t0) of the systolic phase interval (SP) and an end point (tN) of the systolic phase interval (SP)

wherein a QT interval is determined as the start of the Q wave and the end of the T wave in the hearts electrical cycle, and the determination of the end point (tN) of the systolic phase interval (SP) is restricted to the measured points of arterial pressure which fulfill the condition that the difference in time between the end point (tN) to be determined of the systolic phase interval (SP) and the starting point (t0) of the systolic phase interval (SP) is smaller than the QT interval.

In a further embodiment of the invention an apparatus is provided, wherein the end point (tN) of the systolic phase interval (SP) is determined by the processor (15) as the sum of the time interval between the starting point (t0) of the systolic phase interval (SP) and the point of time (tK), where the mean arterial pressure (MAP) is reached for the first time following the starting point (t0) of the systolic phase interval (SP) and the product of a factor (c) with the QT interval (QT), wherein the factor (c) is a value between 0.25 and 0.8, especially wherein the factor (c) fulfills the condition $$c = \sqrt{\frac{SAP - MAP}{SAP - P_0}}$$

with the maximum arterial pressure (SAP) and the mean arterial pressure (MAP) and the base line pressure (P0), which is approximately equal to the pressure within the left ventricle as well as within the left atrium at the time of the start of the Q wave and the end of the T wave in the hearts electrical cycle.

In a further embodiment of the invention an apparatus is provided, wherein the search for the end point (tN) of the systolic phase (SP) is restricted by the processor (15) to the interval between the point of time of the maximum arterial pressure (tM) and the end of the QT interval (tT).

In a further embodiment of the invention an apparatus is provided, wherein the search for the end point (tN) of the systolic phase (SP) is restricted by the processor (15) to the region where the measured arterial pressure is higher than the mean arterial pressure (MAP).

In a further embodiment of the invention an apparatus is provided, wherein the processor (15) is programmed to determine the end point (tN) of the systolic phase interval (SP) by the intersection of two fitted functions with a first function of parabolic nature (y1) and a second function of exponential nature (y2).

In a further embodiment of the invention an apparatus is provided, wherein the first function of parabolic nature (y1) is fitted to the pressure curve defined by the measured pressure curve of the systolic phase and the second function of exponential nature (y2) is fitted to the pressure curve defined by the measured pressure curve of the diastolic phase.

Figure 2:
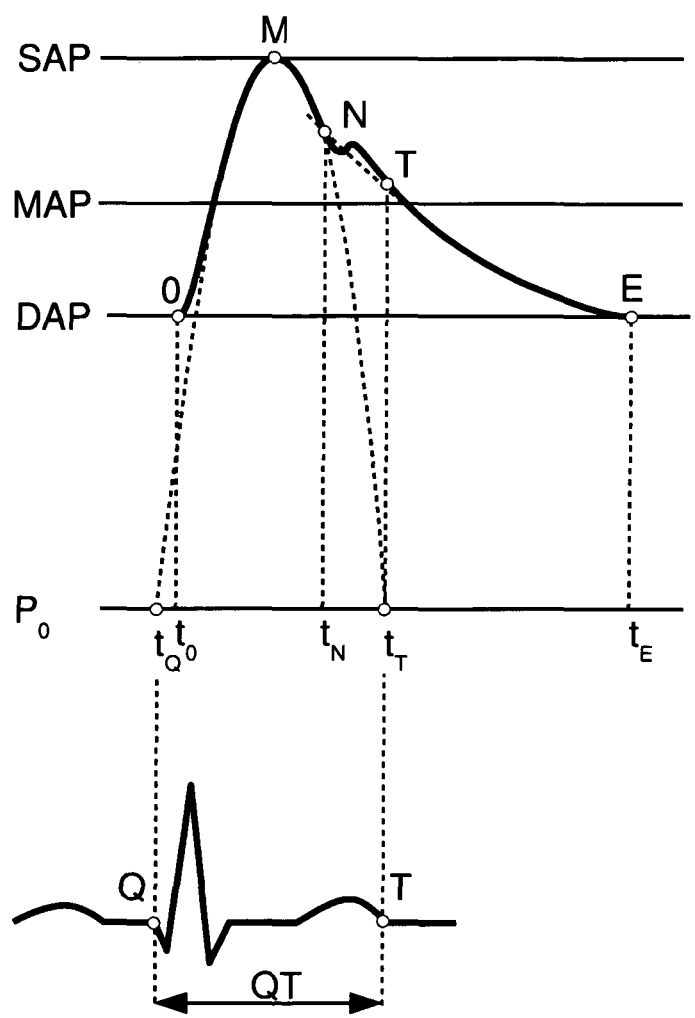
Figure 3:
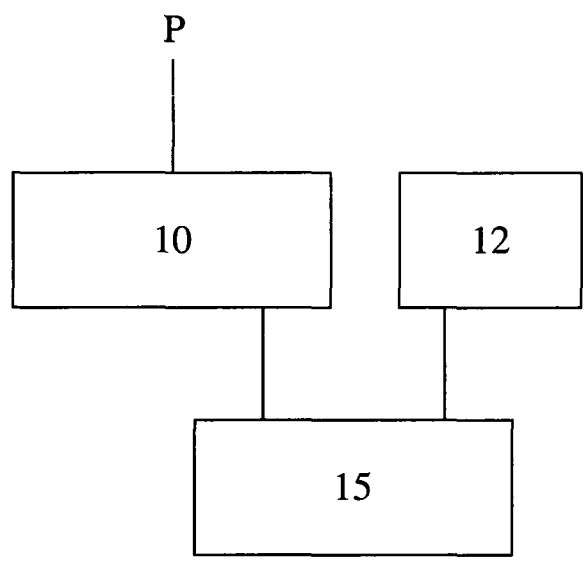

The invention is now described with respect to the figures. In the figures is shown:

FIG. 1 A first graph for the arterial pressure curve,

FIG. 2 a second graph for the arterial pressure curve as well as the QT interval and FIG. 3 an apparatus according to an embodiment of the present invention.

In FIG. 1 a first graph for the arterial pressure curve is shown. The diastolic arterial pressure DAP is shown as the base line of this graph. At the point of time t0, the systolic phase interval starts. The pressure curve then shows higher data since the pressure is increasing until the maximum arterial pressure at point M, i.e. the level of SAP. Between the two levels DAP and SAP is the mean arterial pressure level MAP. The intersection of the mean arterial pressure MAP level and the pressure curve is designated with the letter K when the pressure is ascending and the letter L when the pressure curve is descending. The point of time at the point K is designated as tK. Between the maximum arterial pressure SAP at point M and the mean arterial pressure MAP after descending from SAP there is the point of the dicrotic notch, designated with the letter N. The point of time at this dicrotic notch is named tN. Thus, the systolic phase interval is the time interval between t0 and tN. The point E is the beginning of the next systolic phase interval.

With this, a method is provided, wherein the end point (tN) of the systolic phase interval (SP) is determined as the sum of the time interval between the starting point (t0) of the systolic phase interval (SP) and the point of time (tK), where the mean arterial pressure (MAP) is reached for the first time following the starting point (t0) of the systolic phase interval (SP) and the product of a factor (c) with the QT interval (QT), wherein the factor (c) is a value between 0.25 and 0.8, especially wherein the factor (c) fulfills the condition $$c = \sqrt{\frac{SAP - MAP}{SAP - P_0}}$$

with the maximum arterial pressure (SAP) and the mean arterial pressure (MAP) and the base line pressure (P0), which is approximately equal to the pressure within the left ventricle as well as within the left atrium at the time of the start of the Q wave and the end of the T wave in the hearts electrical cycle. Thus, the factor c corresponds to a parabola function fitted in the curve between the points K and M. As a result, the intersection between this parabola function and the level of MAP can be determined. This point of intersection is used as an approximation for the point N and thus the point of time tN. Thus, the systolic phase interval can be written as:

$$t_N = t_K + c \cdot QT$$

This is a very robust algorithm that tracks parameter changes much better and much more accurately compared to previous algorithms with or without notch detection.

In FIG. 2 a second graph for the arterial pressure curve as well as the QT interval is shown. The same abbreviations and designation numbers are used as in FIG. 1 when appropriate. Further, the base line pressure $P_0$ is shown. At the time of point Q and point T, the pressure within the left ventricle is at the same level $P_0$ as within the left atrium. This pressure could be roughly substituted by an assumed, situation dependent value or roughly substituted by the central venous pressure or by zero. The time interval between tQ and tT corresponds to the QT interval, shown in the second graph at the bottom.

The end of the systolic phase is now estimated more accurately by the following procedure. A function prototype $y_1$ could be fitted to the pressure curve of the systolic phase— from the start of the systolic phase (point 0 at $t_0$) until a preliminary point for the end of the systolic phase (point N at $t_N$). The fitting is done in a way, that the time distance of the curve points at the $P_0$ pressure level becomes equal to the QT interval. Preferably a parallel shifted parabola function is used as function prototype $y_1$ $$y_1 = SAP - 4 \cdot \frac{SAP - CVP}{QT^2} \cdot (t - a)^2$$

The parallel shifting is preferably done with a coordinate transformation $$t \rightarrow t + b \cdot y$$

The parameters a and b are then preferably adjusted to provide the least square of residuals $(AP-y_1)^2$.

Thus, the fitted curve could be regarded as a surrogate for the pressure within the left ventricle.

Another function prototype $y_2$ could be fitted to the pressure curve of the diastolic phase—from end-systolic phase (point N at $t_N$) to beginning of the next systolic phase (point E at $t_E$). The fitting is preferably done in a way that the point N will be on the previously fitted curve $y_1$.

Preferably an exponential decay function is used as function prototype $y_2$.

$$y_2 = CVP + (y_1(t_N) - CVP) \cdot \exp\left(-\frac{t - t_N}{d}\right)$$

The parameter d is then preferably adjusted to provide the least square of residuals $(AP-y_2)^2$.

The preliminary point N for the end-systolic phase is shifted starting from point T until the maximum arterial pressure point M. The final point N for the end of systolic phase will be the one, which gives the best fitting results e.g. the fittings with the least sum of residuals $(AP-y_1)^2 + (AP-y_2)^2$.

In FIG. 3 an apparatus according to an embodiment of the present invention is shown. An input 10 for signals related to a pressure P, especially an arterial pressure is provided as well as a time element 12 to determine the time related to the signals. Further, a processor 15 is provided for computing the systolic phase interval SP of an arterial pressure curve of a heart.

The input 10 for signals P related to a pressure receives data signals with a repetition rate or a scan rate of 4 ms, i.e. approximately 250 data records per second. This data is then processed by the processor 15 according to one of the methods described above in order to determine the systolic phase interval.

REFERENCE SIGNS

10 Signal input
12 Time element
15 Processor
t0 Starting point of the systolic phase interval
tN End point of the systolic phase interval
tQ Start of the Q wave in the hearts electrical cycle
tT End of the T wave in the hearts electrical cycle
tE Beginning of the next systolic phase
SP systolic phase interval
QT QT interval
MAP Mean arterial pressure
SAP Systolic arterial pressure
DAP Diastolic arterial pressure

The invention claimed is:

1. A method for computing a systolic phase interval of an arterial pressure curve, comprising:
    determining, by a processor, a time interval between a starting point ($t_0$) of the systolic phase interval and a time instant ($t_k$), wherein $t_k$ is when a mean arterial pressure is reached for a first time following the starting point ($t_0$);
    calculating, by the processor, a product of a factor and a QT interval, the QT interval being the time between a start of a Q wave and an end of a T wave in an electrical cycle of a heart; and
    summing, by the processor, the time interval and the product to obtain an end point ($t_N$) of the systolic phase interval.

2. The method of claim 1, wherein the factor is a value between 0.25 and 0.8.

3. The method of claim 1, wherein the factor is a square root of $(SAP-MAP)/(SAP-P_0)$, wherein SAP is a maximum arterial pressure, MAP is the mean arterial pressure, and $P_0$ is a base line pressure.

4. An apparatus comprising:
    an input port to receive signals representing an arterial pressure;
    a processor coupled to the input port for computing a systolic phase interval of an arterial pressure curve, the processor adapted to:
        determine a time interval between a starting point ($t_0$) of the systolic phase interval and a time instant ($t_k$), wherein $t_k$ is when a mean arterial pressure is reached for a first time following the starting instant point ($t_0$);
        calculate a product of a factor and a QT interval, the QT interval being the time between a start of a Q wave and an end of a T wave in an electrical cycle of a heart; and
        sum the time interval and the product to obtain an end point ($t_N$) of the systolic phase interval.

5. The apparatus of claim 4, wherein the factor is a value between 0.25 and 0.8.

6. The apparatus of claim 4, wherein the factor is a square root of $(SAP-MAP)/(SAP-P_0)$, wherein SAP is a maximum arterial pressure, MAP is the mean arterial pressure, and $P_0$ is a base line pressure.

* * * * *